US012569271B2

(12) United States Patent
Van Tol et al.

(10) Patent No.: US 12,569,271 B2
(45) Date of Patent: Mar. 10, 2026

(54) SURGICAL INSTRUMENTS, SYSTEMS, AND METHODS INCORPORATING AN ULTRASONIC TRANSDUCER

(71) Applicant: Covidien LP, Mansfield, MA (US)

(72) Inventors: David J. Van Tol, Boulder, CO (US);
Michael B. Lyons, Boulder, CO (US);
Ken Netzel, Loveland, CO (US);
Monte S. Fry, Longmont, CO (US);
James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 231 days.

(21) Appl. No.: 18/566,600

(22) PCT Filed: Jun. 1, 2022

(86) PCT No.: PCT/IB2022/055144
§ 371 (c)(1),
(2) Date: Dec. 1, 2023

(87) PCT Pub. No.: WO2022/259098
PCT Pub. Date: Dec. 15, 2022

(65) Prior Publication Data
US 2024/0358393 A1 Oct. 31, 2024

Related U.S. Application Data

(60) Provisional application No. 63/209,708, filed on Jun. 11, 2021.

(51) Int. Cl.
A61B 17/32 (2006.01)
A61B 17/00 (2006.01)
A61B 34/35 (2016.01)

(52) U.S. Cl.
CPC ................ *A61B 17/320068* (2013.01); *A61B 17/00234* (2013.01); *A61B 34/35* (2016.02);
(Continued)

(58) Field of Classification Search
CPC ........... A61B 2017/320094; A61B 17/320092;
A61B 2017/320071; A61B 17/320068;
(Continued)

(56) References Cited

U.S. PATENT DOCUMENTS 5,792,135 A 8/1998 Madhani et al.
5,897,523 A 4/1999 Wright et al.
(Continued)

FOREIGN PATENT DOCUMENTS

WO 2021006984 A1 1/2021
WO 2021173294 A1 9/2021
(Continued)

OTHER PUBLICATIONS

U.S. Appl. No. 17/970,257, filed Oct. 20, 2022, Inventor: Matthew S. Cowley.
(Continued)

*Primary Examiner* — Katherine M Shi

(57) ABSTRACT

An ultrasonic surgical system includes an ultrasonic transducer configured to receive an electrical drive signal and produce ultrasonic mechanical motion that is output along an ultrasonic horn of the ultrasonic transducer. The ultrasonic horn defines a transverse cam slot. A blade extends from the ultrasonic horn. The blade receives the ultrasonic mechanical motion from the ultrasonic horn for treating tissue. A jaw member is movable relative to the blade between a spaced-apart position and an approximated position for clamping tissue. A cam pin is slidably disposed in the cam slot and is operably coupled to the jaw member. Slidably advancing the cam pin in the cam slot actuates the (Continued)

jaw member between the spaced-apart position and the approximated position.

15 Claims, 8 Drawing Sheets

(52) U.S. Cl.
CPC ............... *A61B 2017/00141* (2013.01); *A61B 2017/00199* (2013.01); *A61B 2017/00353* (2013.01); *A61B 2017/00398* (2013.01); *A61B 2017/00477* (2013.01); *A61B 2017/320071* (2017.08); *A61B 2017/320075* (2017.08); *A61B 2017/320094* (2017.08)

(58) Field of Classification Search
CPC .. A61B 2017/320095; A61B 2017/003; A61B 2017/320074; A61B 2017/2936; A61B 2017/2933; A61B 2017/320075; A61B 2017/320088; A61B 17/2202
See application file for complete search history.

(56) References Cited

U.S. PATENT DOCUMENTS

| | | | |
|---|---|---|---|
| 6,036,667 | A | 3/2000 | Manna et al. |
| 7,135,030 | B2 | 11/2006 | Schwemberger et al. |
| 10,172,636 | B2 | 1/2019 | Stulen et al. |
| 10,226,274 | B2 | 3/2019 | Worrell et al. |
| 10,258,363 | B2 | 4/2019 | Worrell et al. |
| 10,335,182 | B2 | 7/2019 | Stulen et al. |
| 10,405,876 | B2 | 9/2019 | Boudreaux |
| 10,413,316 | B2 | 9/2019 | Lyons |
| 10,492,819 | B2 | 12/2019 | Hibner |
| 10,575,836 | B2 | 3/2020 | Hibner et al. |
| 10,912,581 | B2 | 2/2021 | Stulen et al. |
| 10,925,630 | B2 | 2/2021 | Cuti et al. |
| 10,987,123 | B2 | 4/2021 | Weir et al. |
| 11,337,717 | B2 | 5/2022 | Lyons |
| 2002/0165577 | A1 | 11/2002 | Witt et al. |
| 2006/0058825 | A1 | 3/2006 | Ogura et al. |
| 2006/0190034 | A1 | 8/2006 | Nishizawa et al. |
| 2008/0214967 | A1 | 9/2008 | Aranyi et al. |
| 2009/0163948 | A1 | 6/2009 | Sunaoshi et al. |
| 2013/0012959 | A1 | 1/2013 | Jinno |
| 2013/0140835 | A1 | 6/2013 | Stefanchik |
| 2014/0005701 | A1 | 1/2014 | Olson et al. |
| 2014/0005702 | A1* | 1/2014 | Timm .................... A61B 17/29 606/169 |
| 2014/0135804 | A1 | 5/2014 | Weisenburgh, II et al. |
| 2014/0276931 | A1 | 9/2014 | Parihar et al. |
| 2014/0309562 | A1 | 10/2014 | Ito |
| 2014/0350570 | A1 | 11/2014 | Lee |
| 2015/0080924 | A1 | 3/2015 | Stulen et al. |
| 2016/0302812 | A1 | 10/2016 | Monroe et al. |
| 2017/0202599 | A1* | 7/2017 | Shelton, IV ........ H01M 6/5044 |
| 2019/0021752 | A1 | 1/2019 | Boudreaux |
| 2019/0021756 | A1 | 1/2019 | Boudreaux |
| 2019/0133635 | A1 | 5/2019 | Stulen et al. |
| 2019/0216493 | A1 | 7/2019 | Worrell et al. |
| 2019/0231385 | A1 | 8/2019 | Cowley |
| 2019/0247083 | A1 | 8/2019 | Worrell et al. |
| 2019/0290318 | A1 | 9/2019 | Boudreaux |
| 2019/0321068 | A1 | 10/2019 | Hibner et al. |
| 2019/0321069 | A1 | 10/2019 | Hibner |
| 2019/0321070 | A1 | 10/2019 | Boudreaux |
| 2019/0380735 | A1 | 12/2019 | Cuti et al. |
| 2020/0229833 | A1 | 7/2020 | Vakharia et al. |
| 2020/0229834 | A1 | 7/2020 | Olson et al. |
| 2020/0237397 | A1 | 7/2020 | Boudreaux |
| 2020/0237399 | A1 | 7/2020 | Stulen et al. |
| 2021/0353324 | A1 | 11/2021 | Fagan et al. |
| 2021/0353325 | A1 | 11/2021 | Fagan et al. |
| 2021/0369295 | A1 | 12/2021 | Cowley |
| 2022/0249110 | A1 | 8/2022 | Lyons |
| 2023/0095787 | A1 | 3/2023 | Fagan et al. |

FOREIGN PATENT DOCUMENTS

| | | | |
|---|---|---|---|
| WO | 2021178103 | A1 | 9/2021 |
| WO | 2021202035 | A1 | 10/2021 |

OTHER PUBLICATIONS

International Search Report and Written Opinion issued in corresponding International Application No. PCT/IB2022/055144 mailed Aug. 26, 2022, 9 pages.

* cited by examiner

SURGICAL INSTRUMENTS, SYSTEMS, AND METHODS INCORPORATING AN ULTRASONIC TRANSDUCER

CROSS-REFERENCE TO RELATED APPLICATION

This application is a 371 National Stage Application of International Application No. PCT/IB2022/055144, filed Jun. 1, 2022, which claims the benefit of, and priority to, U.S. Provisional Patent Application No. 63/209,708, filed on Jun. 11, 2021, the entire contents of each of which are hereby incorporated herein by reference.

FIELD

The present disclosure relates to energy-based surgical instruments and, more particularly, to surgical instruments, systems, and methods incorporating an ultrasonic transducer.

BACKGROUND

Surgical instruments and systems incorporating ultrasonic functionality utilize ultrasonic energy, i.e., ultrasonic vibrations, to treat tissue. More specifically, mechanical vibration energy transmitted at ultrasonic frequencies can be utilized to treat, e.g., seal and transect, tissue. A surgical instrument incorporating ultrasonic functionality may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

SUMMARY

Provided in accordance with aspects of the disclosure is an ultrasonic surgical system including an ultrasonic transducer configured to receive an electrical drive signal and produce ultrasonic mechanical motion that is output along an ultrasonic horn of the ultrasonic transducer. The ultrasonic horn defines a cam slot. A blade extends from the ultrasonic horn. The blade receives the ultrasonic mechanical motion from the ultrasonic horn for treating tissue. A jaw member is movable relative to the blade between a spaced-apart position and an approximated position for clamping tissue. A cam pin is slidably disposed in the cam slot and is operably coupled to the jaw member. Slidably advancing the cam pin in the cam slot actuates the jaw member between the spaced-apart position and the approximated position.

According to aspects of the disclosure, at least one transverse hole is defined in the ultrasonic horn. A pivot pin is disposed in the transverse hole. The pivot pin operably couples the jaw member to the blade.

According to aspects of the disclosure, a second transverse hole is formed in the ultrasonic horn. The second transverse hole is configured to balance a transmission of the ultrasonic mechanical motion through the ultrasonic horn.

According to aspects of the disclosure, the second transverse hole is laterally offset with respect to the cam slot.

According to aspects of the disclosure, the second transverse hole is laterally offset with respect to the first transverse hole.

According to aspects of the disclosure, the ultrasonic transducer defines a central axis. The second transverse hole is laterally offset from the first transverse hole and the cam slot with respect to the central axis of the ultrasonic transducer.

According to aspects of the disclosure, the cam slot defines a proximal side and a distal side. The first transverse hole is positioned distal of the distal side of the cam slot and the second transverse hole is positioned proximal of the proximal side of the cam slot.

According to aspects of the disclosure, the first transverse hole is positioned on a first side of the central axis and the second transverse hole is positioned on a second side of the central axis opposite the first side.

According to aspects of the disclosure, an elongated assembly supports the ultrasonic transducer. The elongated assembly defines at least one articulation joint. The ultrasonic transducer is positioned at a distal side of the at least one articulation joint.

According to aspects of the disclosure, the ultrasonic generator is positioned at the distal side of the at least one articulation joint.

According to aspects of the disclosure, the ultrasonic transducer, the blade, the jaw, and the cam pin form at least a portion of an end effector assembly configured to connect to a robotic arm of a robotic surgical system.

According to aspects of the disclosure, the ultrasonic transducer includes a piezoelectric stack maintained in pre-compression against the ultrasonic horn. The piezoelectric stack may be maintained in pre-compression directly between a proximal end mass and the ultrasonic horn.

According to aspects of the disclosure, the blade extends directly from the ultrasonic horn. Alternatively, a waveguide is disposed between the ultrasonic horn and the blade.

BRIEF DESCRIPTION OF THE DRAWINGS

The above and other aspects and features of the present disclosure will become more apparent in light of the following detailed description when taken in conjunction with the accompanying drawings.

DETAILED DESCRIPTION

Figure 1:
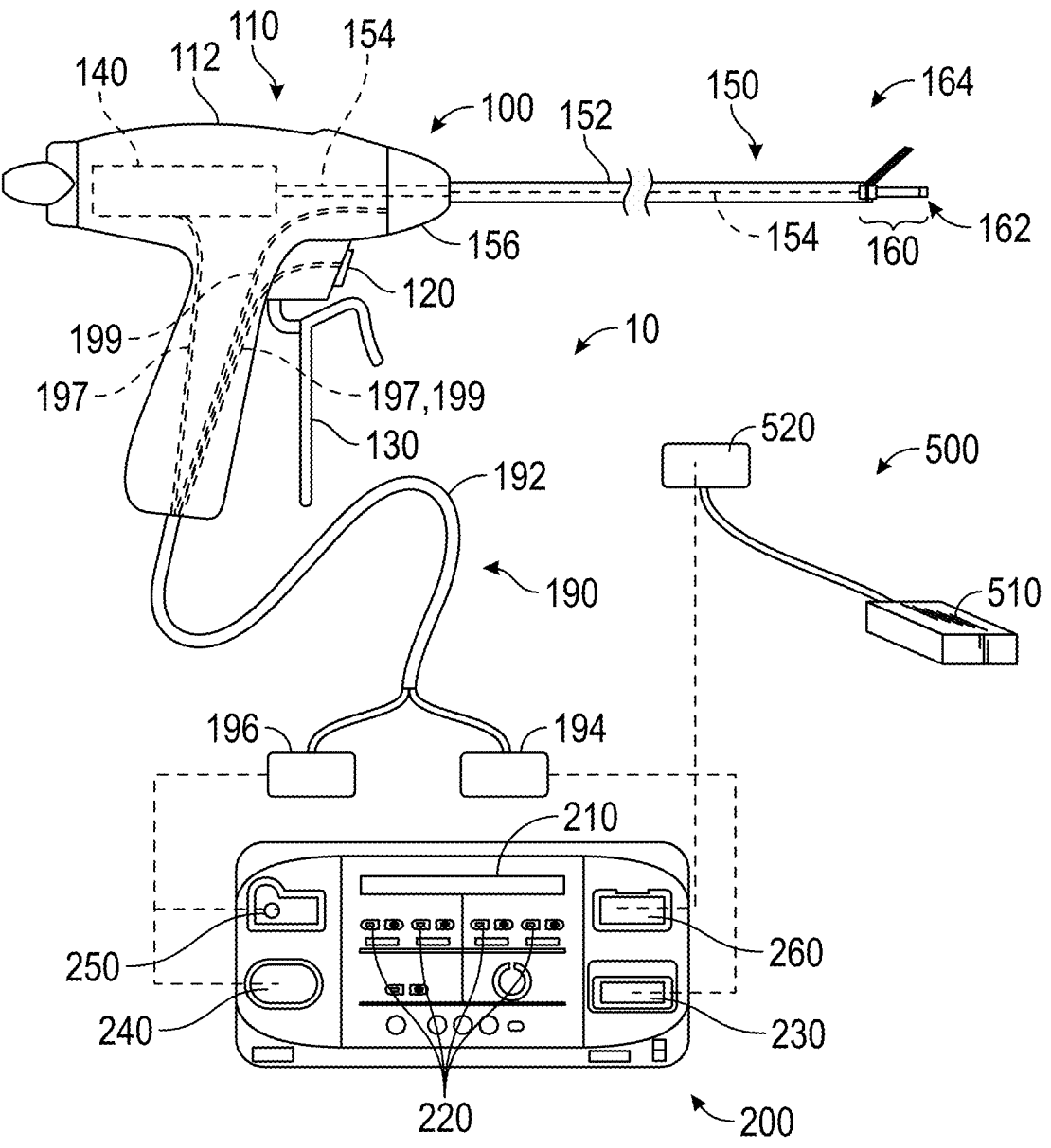
FIG. 1 is a side view of a surgical system provided in accordance with the present disclosure including a surgical instrument, a surgical generator, and a return electrode device.

As used herein, the term "distal" refers to the portion that is being described which is further from an operator (whether a human surgeon or a surgical robot), while the term "proximal" refers to the portion that is being described which is closer to an operator. Further, to the extent consistent, any of the aspects and features detailed herein may be used in conjunction with any or all of the other aspects and features detailed herein.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Referring to FIG. 1, a surgical system provided in accordance with aspects of the present disclosure is shown generally identified by reference numeral 10 including a surgical instrument 100, a surgical generator 200, and, in some aspects, a return electrode device 500, e.g., including a return pad 510. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200.

Surgical generator 200 includes a display 210, a plurality user interface features 220, e.g., buttons, touch screens, switches, etc., an ultrasonic plug port 230, a bipolar electrosurgical plug port 240, and active and return monopolar electrosurgical plug ports 250, 260, respectively. As an alternative to plural dedicated ports 230-260, one or more common ports (not shown) may be configured to act as any two or more of ports 230-260.

Surgical instrument 100 is configured to operate in one or more electrosurgical modes supplying Radio Frequency (RF) energy to tissue to treat tissue, e.g., a monopolar configuration and/or a bipolar configuration, and an ultrasonic mode supplying ultrasonic energy to tissue to treat tissue. The modes may operate simultaneously, sequentially, or in any other suitable manner. Surgical generator 200 is configured to produce ultrasonic drive signals for output through ultrasonic plug port 230 to surgical instrument 100 to activate surgical instrument 100 in the ultrasonic mode and to provide electrosurgical energy, e.g., RF bipolar energy for output through bipolar electrosurgical plug port 240 and/or RF monopolar energy for output through active monopolar electrosurgical port 250 to surgical instrument 100 to activate surgical instrument 100 in the one or more electrosurgical modes. Plug 520 of return electrode device 500 is configured to connect to return monopolar electrosurgical plug port 260 to return monopolar electrosurgical energy from surgical instrument 100 in the monopolar electrosurgical mode. In other aspects, the electrosurgical functionality (and associated components and configurations) of surgical instrument 100 may be omitted such that surgical instrument 100 operates only in an ultrasonic mode.

Continuing with reference to FIG. 1, handle assembly 110 includes a housing 112, an activation button 120, and a clamp trigger 130. Housing 112 is configured to support an ultrasonic transducer 140. Ultrasonic transducer 140 may be permanently engaged within housing 112 or removable therefrom. Ultrasonic transducer 140 includes a piezoelectric stack or other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. Feedback and/or control signals may likewise be communicated between ultrasonic transducer 140 and surgical generator 200. Ultrasonic transducer 140, more specifically, and as detailed below, may include a stack of piezoelectric elements secured, under pre-compression between proximal and distal end masses or a proximal end mass and an ultrasonic horn with first and second electrodes electrically coupled between piezoelectric elements of the stack of piezoelectric elements to enable energization thereof to produce ultrasonic energy. However, other suitable ultrasonic transducer configurations, including plural transducers and/or non-longitudinal, e.g., torsional, transducers are also contemplated.

An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting (such as a LOW power or tissue scaling setting) and a second actuated position corresponding to a second activation setting (such as a HIGH power or tissue transection setting). In still other configurations, separate activation buttons may be provided, e.g., a first actuation button for activating a first activation setting and a second activation button for activating a second activation setting. Additional activation buttons, sliders, wheels, etc. are also contemplated to enable control of various different activation settings from housing 112.

Elongated assembly 150 of surgical instrument 100 includes an outer drive sleeve 152, a waveguide 154, a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164. Advancing the outer drive sleeve 152 actuates the jaw member 164 between open and clamped configurations. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although non-conductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. In configurations where surgical instrument 100 is only configured for ultrasonic operation, electrosurgical plug 196 and associated components are omitted.

Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, and where electrosurgical functionality is provided, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that bipolar electrosurgical energy may be conducted between blade 162 and jaw member 164 (and/or between different portions of jaw member 164). In monopolar configurations, a second electrical lead wire 199 is electrically coupled to waveguide 154 such that monopolar electrosurgical energy may be supplied to tissue from blade 162. Alternatively, or additionally, a second electrical lead wire 199 may electrically couple to jaw member 164 in the monopolar configuration to enable monopolar electrosurgical energy to be supplied to tissue from jaw member 164. In configurations where both bipolar and monopolar functionality are enabled, one or more of the second electrical lead wires 199 may be used for both the delivery of bipolar energy and monopolar energy; alternatively, bipolar and monopolar energy delivery may be provided by separate second electrical lead wires 199. One or more other second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode.

Figure 2:
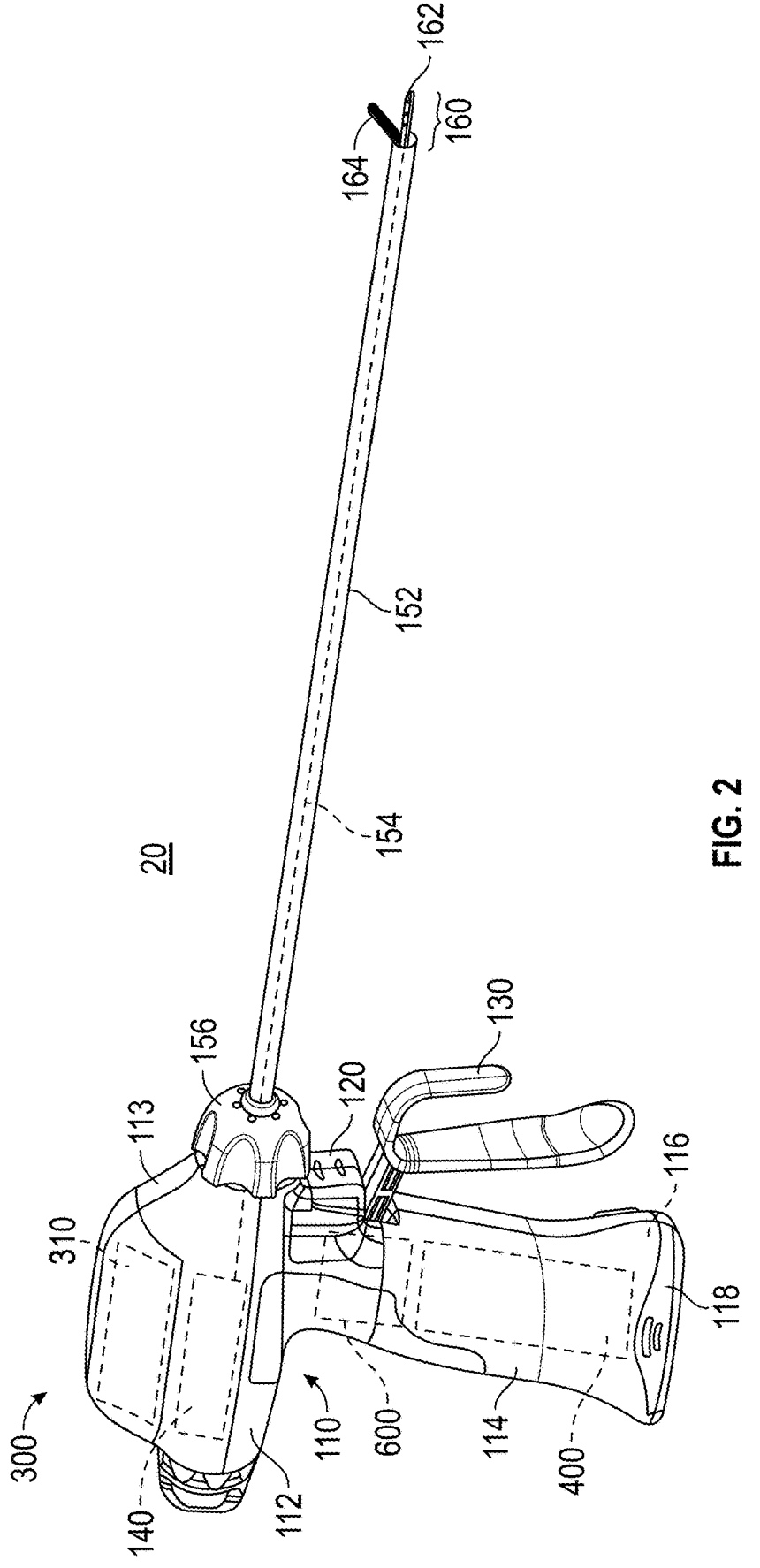
FIG. 2 is a perspective view of another surgical system provided in accordance with the present disclosure including a surgical instrument incorporating an ultrasonic generator, electrosurgical generator, and power source therein.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated. More specifically, with reference to FIG. 2, another surgical system in accordance with the present disclosure is shown illustrated as a surgical instrument 20 supporting an ultrasonic generator 310, a power source (e.g., battery assembly 400), and an electrosurgical generator 600 thereon or therein. Surgical instrument 20 is similar to surgical instrument 100 (FIG. 1) and may include any of the features thereof except as explicitly contradicted below. Accordingly, only differences between surgical instrument 20 and surgical instrument 100 (FIG. 1) are described in detail below while similarities are omitted or summarily described.

Housing 112 of surgical instrument 20 includes a body portion 113 and a fixed handle portion 114 depending from body portion 113. Body portion 113 of housing 112 is configured to support an ultrasonic transducer and generator assembly ("TAG") 300 including ultrasonic generator 310 and ultrasonic transducer 140. TAG 300 may be permanently engaged with body portion 113 of housing 112 or removable therefrom.

Fixed handle portion 114 of housing 112 defines a compartment 116 configured to receive battery assembly 400 and electrosurgical generator 600 and a door 118 configured to enclose compartment 116. An electrical connection assembly (not shown) is disposed within housing 112 and serves to electrically couple activation button 120, ultrasonic generator 310 of TAG 300, and battery assembly 400 with one another when TAG 300 is supported on or in body portion 113 of housing 112 and battery assembly 400 is disposed within compartment 116 of fixed handle portion 114 of housing 112, thus enabling activation of surgical instrument 20 in an ultrasonic mode in response to appropriate actuation of activation button 120. Further, the electrical connection assembly or a different electrical connection assembly disposed within housing 112 serves to electrically couple activation button 120, electrosurgical generator 600, battery assembly 400, and end effector assembly 160 (e.g., blade 162 and jaw member 164 and/or different portions of jaw member 164) with one another when electrosurgical generator 600 and battery assembly 400 are disposed within compartment 116 of fixed handle portion 114 of housing 112, thus enabling activation of surgical instrument 20 in an electrosurgical mode, e.g., bipolar RF, in response to appropriate actuation of activation button 120. For a monopolar electrosurgical mode, return electrode device 500 (FIG. 1) may be configured to connect to surgical instrument 20 (electrosurgical generator 600 thereof, more specifically), to complete a monopolar circuit through tissue and between surgical instrument 30 (e.g., blade 162 and/or jaw member 164) and return electrode device 500 (FIG. 1).

Figure 3A:
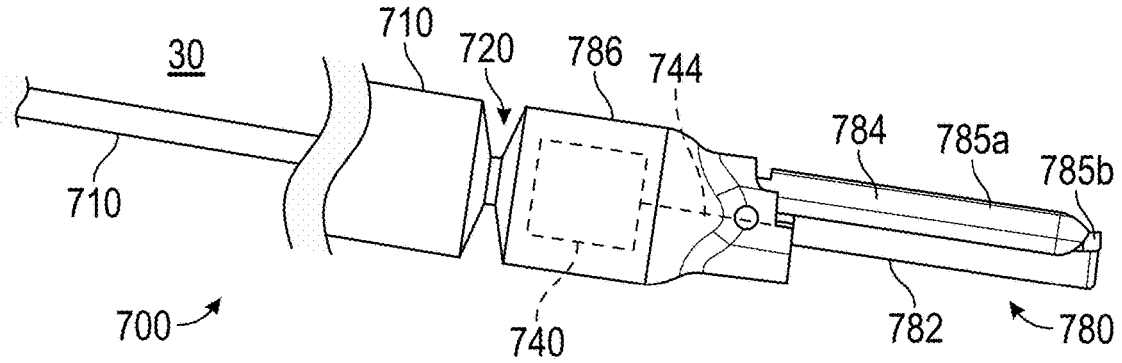
FIGS. 3A and 3B are perspective views of a distal portion of still another surgical instrument provided in accordance with the present disclosure with a distal end portion thereof enlarged and an end effector assembly thereof disposed in un-articulated and articulated positions, respectively.
Figure 3B:
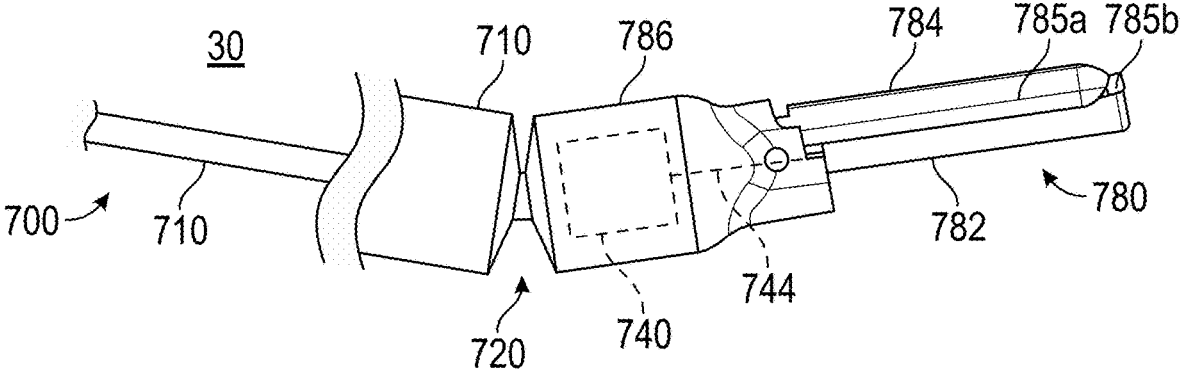

With reference to FIGS. 3A and 3B, a distal portion of another surgical instrument 30 provided in accordance with the present disclosure is shown. Surgical instrument 30 may be configured similar to and include any of the features of surgical instrument 100 (for use with a remote generator 200 as part of system 10) (FIG. 1) or surgical instrument 20 (including ultrasonic and electrosurgical generators 310, 600 and a battery assembly 400 thereon or therein) (FIG. 2), except as explicitly contradicted below. Accordingly, only differences between surgical instrument 30 and surgical instruments 100, 20 (FIGS. 1 and 2, respectively) are described in detail below while similarities are omitted or summarily described.

Surgical instrument 30 includes a housing (not shown, for manual manipulation or attachment to a surgical robot) and an elongated assembly 700 extending distally from the housing. Elongated assembly 700 of surgical instrument 30 includes an elongated shaft 710 having one or more articulating portions 720, an ultrasonic transducer 740, and an end effector assembly 780 including a blade 782, a jaw member 784, and a distal housing 786.

Elongated shaft 710, as noted above, extends distally from the housing. The one or more articulating portions 720 are disposed along at least a portion of elongated shaft 710. More specifically, an articulating portion 720 is shown in FIGS. 3A and 3B in the form of an articulating joint disposed at a distal end portion of elongated shaft 710 and coupled to distal housing 786 of end effector assembly 780 such that articulation of articulating portion 720 relative to a longitudinal axis of elongated shaft 710 articulates end effector assembly 780 relative to the longitudinal axis of elongated shaft 710. However, it is also contemplated that additional or alternative articulating portions may be disposed along some or all of elongated shaft 710 periodically, intermittently, or continuously (for a portion or the entirety of elongated shaft 710). Each articulating portion 720 may include one or more articulation joints, linkages, flexible portions, malleable portions, and/or other suitable articulating structures to enable articulation of end effector assembly 780 relative to the longitudinal axis of elongated shaft 710 in at least one direction, e.g., pitch articulation and/or yaw articulation. In configurations, the one or more articulating portions 720 are configured to enable both pitch articulation and yaw articulation; in other configurations, unlimited articulation in any direction is enabled.

Jaw member 784 is pivotably mounted on and extends distally from distal housing 786. A drive assembly (not shown) of surgical instrument 30 operably couples the actuator, e.g., clamp trigger 130 (FIG. 1), with jaw member 784 of end effector assembly 780 by way of a jaw drive (not shown) such that the actuator is selectively actuatable to pivot jaw member 784 relative to distal housing 786 and blade 782 of end effector assembly 780 from an open position to a clamping position for clamping tissue between jaw member 784 and blade 782. The jaw drive may include one or more drive shafts, drive sleeves, drive cables, gears, cams, and/or other suitable components. Jaw member 784 includes a more-rigid structural body 785a, which is pivotably mounted on a distal end portion of distal housing 786, and a more-compliant jaw liner 785b, which is captured by the more-rigid structural body 785b and positioned to oppose blade 782 to enable clamping of tissue therebetween.

In configurations where surgical instrument 30 also includes electrosurgical functionality (e.g., bipolar RF and/or monopolar RF), electrical lead wires (not shown) extend through elongated shaft 710 and articulating portion 720 to electrically coupled to ultrasonic horn 744 or blade 782, and/or to jaw member 784 such that bipolar electrosurgical energy may be conducted between blade 782 and jaw member 784 (and/or between different portions of jaw member 784) and/or such that monopolar electrosurgical energy may be supplied to tissue from blade 782 and/or jaw member 784.

An articulation assembly (not shown) including gears, pulleys, sleeves, cables, etc. operably couples a proximal articulation actuator (not shown) with articulating portion 720 such that actuation of the proximal articulation actuator manipulates articulating portion 720 to thereby articulate end effector assembly 780 relative to the longitudinal axis of elongated shaft 710.

Continuing with reference to FIGS. 3A and 3B, an ultrasonic transducer 740 is disposed within distal housing 786 and positioned distally of articulating portion 720, an ultrasonic horn 744 extends distally from ultrasonic transducer 740, and blade 782 extends distally from ultrasonic horn 744. Thus, in contrast to surgical instruments 100, 20 (FIGS. 1 and 2, respectively), ultrasonic transducer 740 is disposed within distal housing 786 distally of articulating portion 720 rather than proximally in the housing of the instrument. Alternatively, ultrasonic transducer 740 may be positioned proximally of articulating portion 720 (in the housing or otherwise positioned), and a waveguide (not shown) including one or more articulating portions, e.g., flexible portions, joint portions, linkage portions, etc., may extend through articulating portion 720 and interconnect ultrasonic transducer 740 with blade 782 such that ultrasonic energy produced by ultrasonic transducer 740 can be transmitted along the waveguide to blade 782 regardless of the articulation of articulating portion 720.

In some configurations, distal housing 786, including ultrasonic transducer 740 therein, defines an outer diameter less than about 15 mm, less than about 12 mm, less than about 10 mm, less than about 8 mm, less than about 5 mm, or less than about 3 mm. As such, ultrasonic transducer 740, in such configurations, may define a sufficiently small diameter (for example, 10% less than the diameters above) so as to enable operable receipt within distal housings 786 of the above-noted dimensions, respectively. By providing a configuration with the above-noted outer diameters, surgical instrument 30 may be utilized minimally-invasively through standard sizes of access devices. Ultrasonic transducer 740, other than its overall size, may be configured similar to ultrasonic transducer 140 (FIG. 1) or any other suitable ultrasonic transducer. For example, ultrasonic transducer 740 may include a stack of piezoelectric elements secured, under pre-compression between a proximal end mass and ultrasonic horn 744 with first and second electrodes electrically coupled between piezoelectric elements of the stack of piezoelectric elements to enable energization thereof to produce ultrasonic energy. Electrical lead wires (not shown) connect the electrodes of ultrasonic transducer 740 with an ultrasonic generator (not shown) to enable an electrical drive signal generated by the ultrasonic generator to be imparted to the stack of piezoelectric elements of ultrasonic transducer 740 to energize the stack of piezoelectric elements to produce ultrasonic energy for transmission to blade 782 via ultrasonic horn 744.

Figure 4:
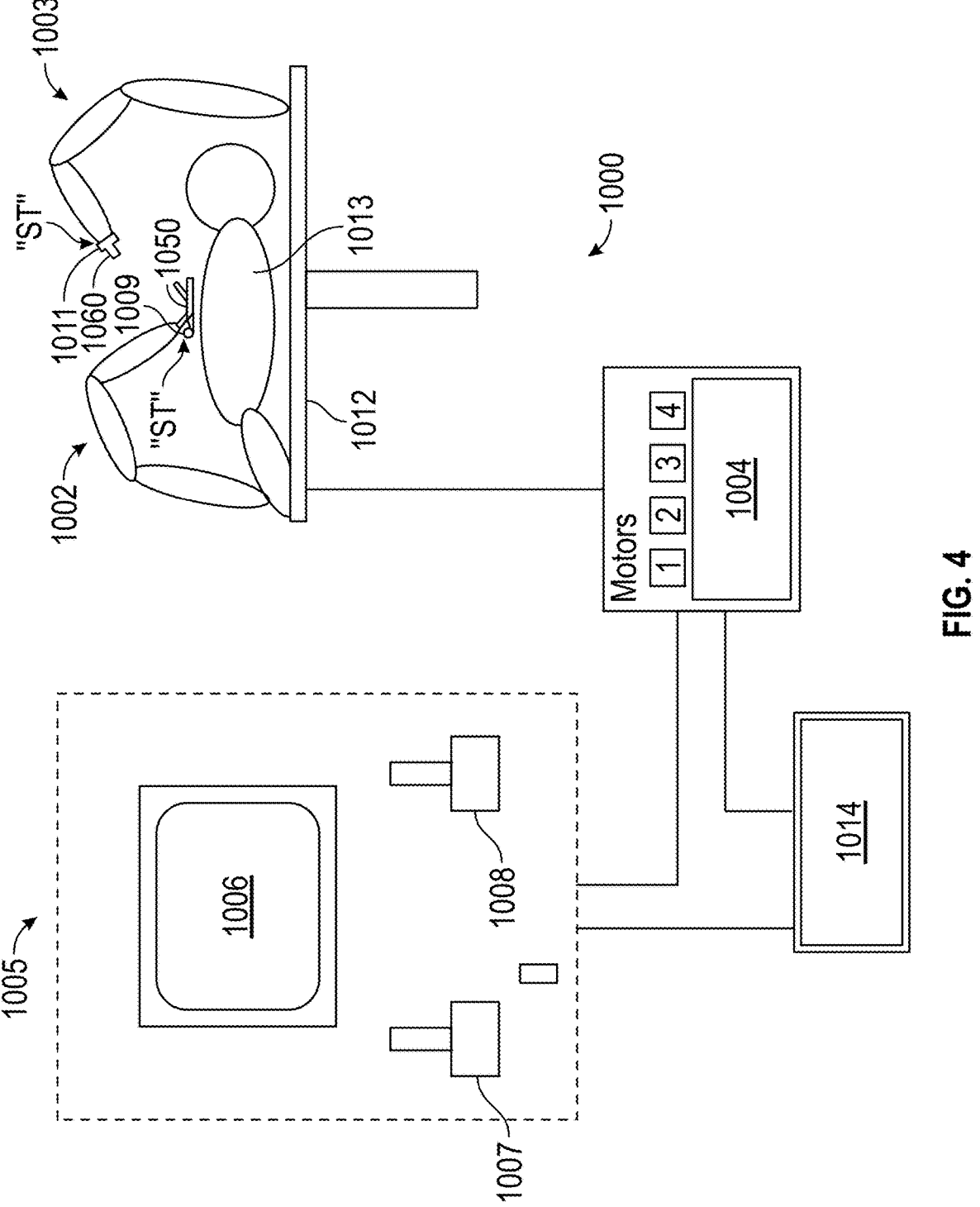
FIG. 4 is a schematic illustration of a robotic surgical system provided in accordance with the present disclosure.

Turning to FIG. 4, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be surgical instrument 100 (FIG. 1), surgical instrument 20 (FIG. 2), or surgical instrument 30 (FIGS. 3A and 3B), e.g., configured for use in both an ultrasonic mode and one or more electrosurgical (bipolar and/or monopolar) modes, wherein manual actuation features, e.g., actuation button 120 (FIG. 1), clamp lever 130 (FIG. 1), the proximal articulation actuator, etc., are replaced with robotic inputs. In such configurations, robotic surgical system 1000 may include or be configured to connect to an ultrasonic generator, an electrosurgical generator, and/or a power source. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
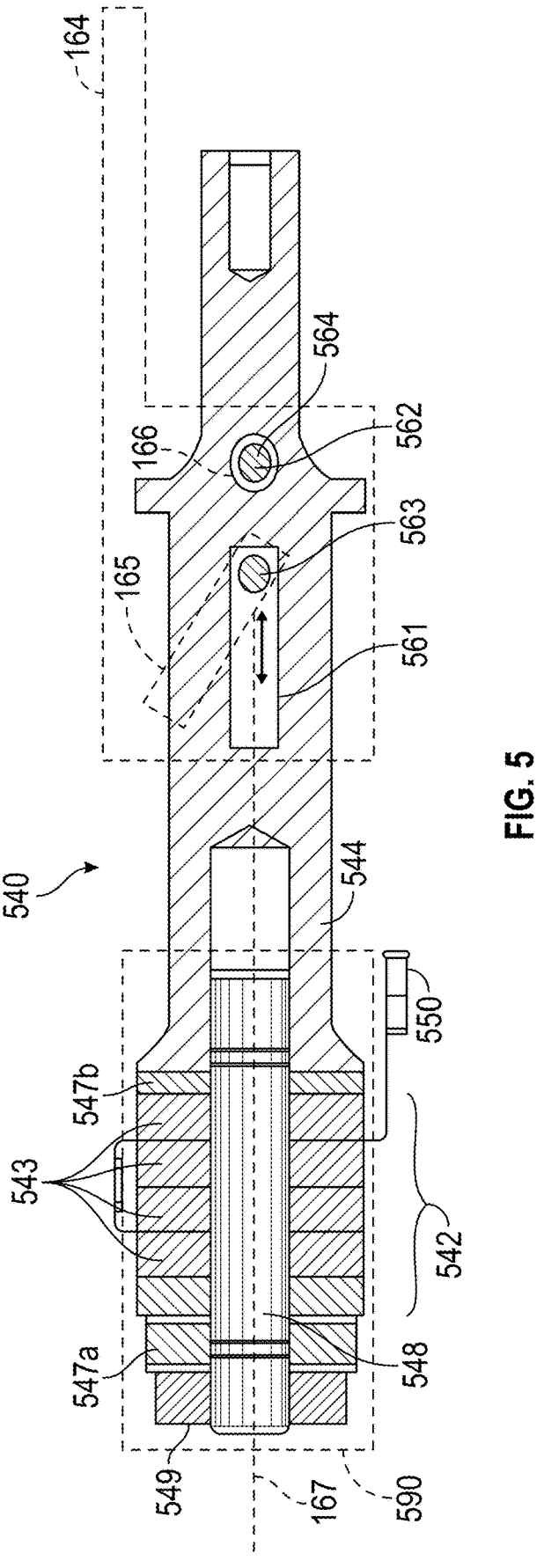
FIG. 5 is a longitudinal, cross-sectional view of an ultrasonic transducer, along with a jaw member shown in phantom, provided in accordance with the present disclosure and configured for use with the surgical systems of FIGS. 1-4 or any other suitable surgical system.

Referring to FIG. 5, an exemplary ultrasonic transducer 540 is provided which may be used as ultrasonic transducer 140 (FIGS. 1 and 2), ultrasonic transducer 740 (FIGS. 3A and 3B), or the ultrasonic transducer of any other suitable surgical instrument. Ultrasonic transducer 540 include a piezoelectric stack 542, ultrasonic horn 544, a proximal end mass 547a, in some aspects a distal end mass 547b (although in other aspects distal end mass 547b is excluded), and a rod 548 securing piezoelectric stack 542 between proximal and distal end masses 547a, 547b, respectively, and to horn 544 under compression. Rod 548 may be secured via a proximal nut 549 threaded or otherwise engaged about rod 548 at a proximal end portion thereof and may be secured distally within a cavity defined within horn 544 via welding, threaded engagement, or in any other suitable manner. The pre-compression of piezoelectric stack 542 against horn 544 (directly or indirectly), enables efficient and effective transmission of ultrasonic energy from piezoelectric stack 542 to horn 544 for transmission along a waveguide to a blade (see FIGS. 1 and 2, for example) or directly from horn 544 to a blade (see FIGS. 3A and 3B, for example). In some configurations, distal end mass 547a is omitted and horn 544 acts as the distal end mass against which piezoelectric stack 542 is directly compressed.

Ultrasonic transducer 540 further includes electrode assembly 550 having at least one electrode disposed in contact with a surface of at least one piezoelectric element 543 of piezoelectric stack 542 and at least one electrode disposed in contact with an opposed surface of the at least one piezoelectric element 543 of piezoelectric stack 542 to, as noted above, enable an electrical input drive signal, e.g., a drive signal voltage, to be applied across piezoelectric stack 542.

In aspects of the present disclosure, a cooling system 590, e.g., including one or more passive cooling devices (such as heat sinks) and/or one or more active cooling devices (such as cooling fluid circulation systems, Peltier coolers, etc.), may be provided to reduce the temperature of piezoelectric elements 543 during operation.

In an ultrasonic surgical instrument (e.g., instrument 100 (FIG. 1)), as described herein, ultrasonic transducer 540 is configured to receive an electrical drive signal and produce ultrasonic mechanical motion that is output along ultrasonic horn 544 of the ultrasonic transducer 540. The ultrasonic horn 544 defines a transverse cam slot 561 and at least one transverse hole 562. A blade (e.g., blade 162 (not shown in FIG. 5, see FIG. 1)) extends from the ultrasonic horn 544. The blade 162 (FIG. 1) receives the ultrasonic mechanical motion from the ultrasonic horn 544 for treating tissue. A jaw member (e.g., jaw member 164) is movable relative to the blade 162 (FIG. 1) between a spaced-apart position and an approximated position for clamping tissue. A cam pin 563 is slidably disposed in the cam slot 561 of ultrasonic horn 544 and in a corresponding cam slot 165 defined in a proximal support portion of the jaw member 164. Slidably advancing the cam pin 563 in the cam slots 561, 165 actuates the jaw member 164 between the spaced-apart position and the approximated position, depending upon the direction of sliding. In aspects, a suitable drive structure, e.g., a drive bar 167, is engaged with or otherwise coupled to cam pin 563 to enable the selective sliding of cam pin 563 upon translation of the drive bar 167. A pivot pin 564 is disposed in the transverse hole 562 and a corresponding transverse hole 166 defined in jaw member 164. The pivot pin 564 thus pivotably couples the jaw member 164 to the ultrasonic horn 544 and, thus, relative to the blade 162 (FIG. 1).

Forming of the cam slot 561 and the transverse hole 562 in the ultrasonic horn 544 reduces an amount of space needed to house the ultrasonic transducer 540 while still supporting the blade 162 and jaw member 164 (see FIG. 1) when the ultrasonic transducer 540 is supported at a distal end portion of an elongated member (e.g., elongated member 710). This arrangement is particularly useful when an ultrasonic surgical instrument is robotically operated without a handle assembly. As an example, the ultrasonic transducer 540 may be housed distal of an articulating portion 720 of elongated member 710, such as in distal housing 786 (see, e.g., FIGS. 3A and 3B). In aspects where the ultrasonic transducer 540 is disposed within a proximal housing, the cam slots and transverse holes detailed above may be defined through the waveguide or proximal portion of the blade rather than the ultrasonic horn 544 of the ultrasonic transducer 540.

As an example, the cam slot 561 (or cam slot 165) may have a curved profile when viewed in longitudinal cross section. The curved profile can be used to facilitate smooth pivoting of the jaw member 164 between spaced-apart and approximated positions as the cam pin 563 is longitudinally advanced therethrough, and to inhibit binding. The curved cam profile can also allow the jaw force to be tuned/optimized throughout the moving jaw/blade range of the cam slot 561.

While the ultrasonic horn 544 is shown and described as having both a cam slot 561 and a transverse hole 562, the cam slot 561 may be omitted, and the jaw member 164 may be actuated by an external sleeve, such as drive sleeve 152 (FIG. 1). In this arrangement the transverse hole(s) described herein would still be formed in the ultrasonic horn 544.

Figure 6:
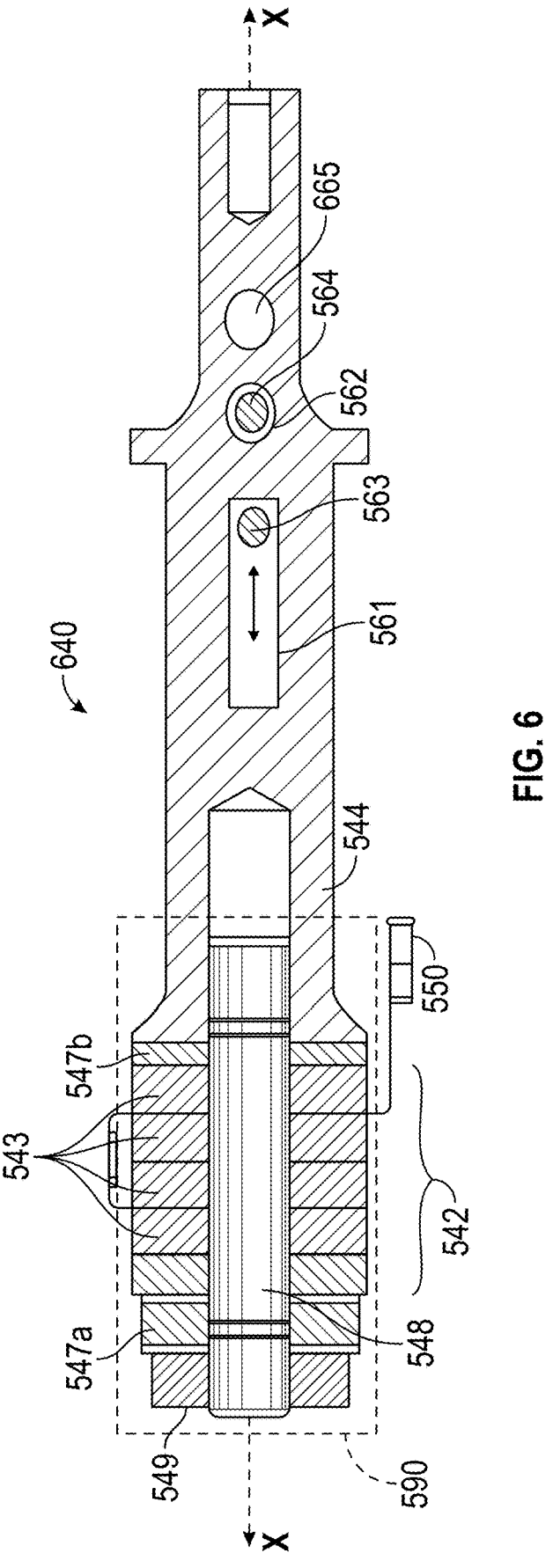
FIG. 6 is a longitudinal, cross-sectional view of another ultrasonic transducer provided in accordance with the present disclosure and configured for use with the surgical systems of FIGS. 1-4 or any other suitable surgical system.

Referring to FIGS. 6, in ultrasonic transducer 640 a second transverse hole 665 is formed in the ultrasonic horn 544. The second transverse hole 665 is configured to mechanically balance a transmission of the ultrasonic mechanical motion through the ultrasonic horn 544. As an example, undesired asymmetric vibration may be reduced or eliminated by the second transverse hole 665. Asymmetric vibration is more likely to occur when a cam slot (e.g., 561 or 562) is off-center. Thus, balancing features described herein may be omitted when the cam slot is centered (e.g., with respect to a central axis (X-X) of the ultrasonic transducer 640. While transverse holes are described below, other balancing features such as adding or removing material from an ultrasonic horn (e.g., indents, recesses, slots and/or protrusions) may be employed to balance vibrations, such as longitudinal vibrations in an ultrasonic horn of ultrasonic transducer 640 or the other ultrasonic transducers described herein.

The second transverse hole 665 may be longitudinally aligned with the cam slot 561. The second transverse hole 665 may also be longitudinally aligned with the first transverse hole 562. For example, the ultrasonic transducer 640 defines a central axis (e.g., axis X-X). The second transverse hole 665 is longitudinally aligned with the first transverse hole 562 and the cam slot 561 along the central axis X-X of the ultrasonic transducer 640.

Figure 7:
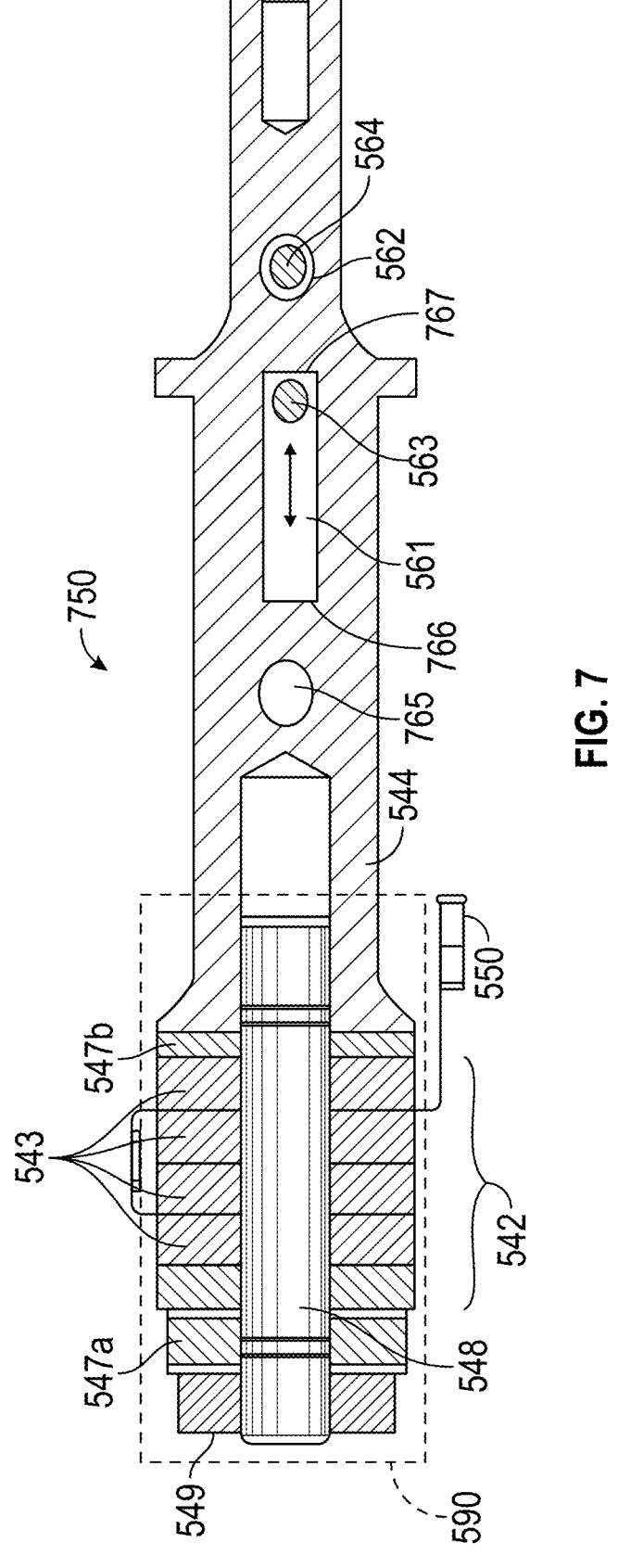
FIG. 7 is a longitudinal, cross-sectional view of another ultrasonic transducer provided in accordance with the present disclosure and configured for use with the surgical systems of FIGS. 1-4 or any other suitable surgical system.

Referring to FIG. 7, in ultrasonic transducer 750 the cam slot 561 defines a proximal side 766 and a distal side 767. The first transverse hole 562 is positioned distal of the distal side 767 of the cam slot 561 and a second transverse hole 765 is positioned proximal of the proximal side 766 of the cam slot 561. The first transverse hole 562 and the second transverse hole 765 may be symmetrically spaced apart from the opposite sides (766, 767, respectively) of the cam slot 561.

Figure 8:
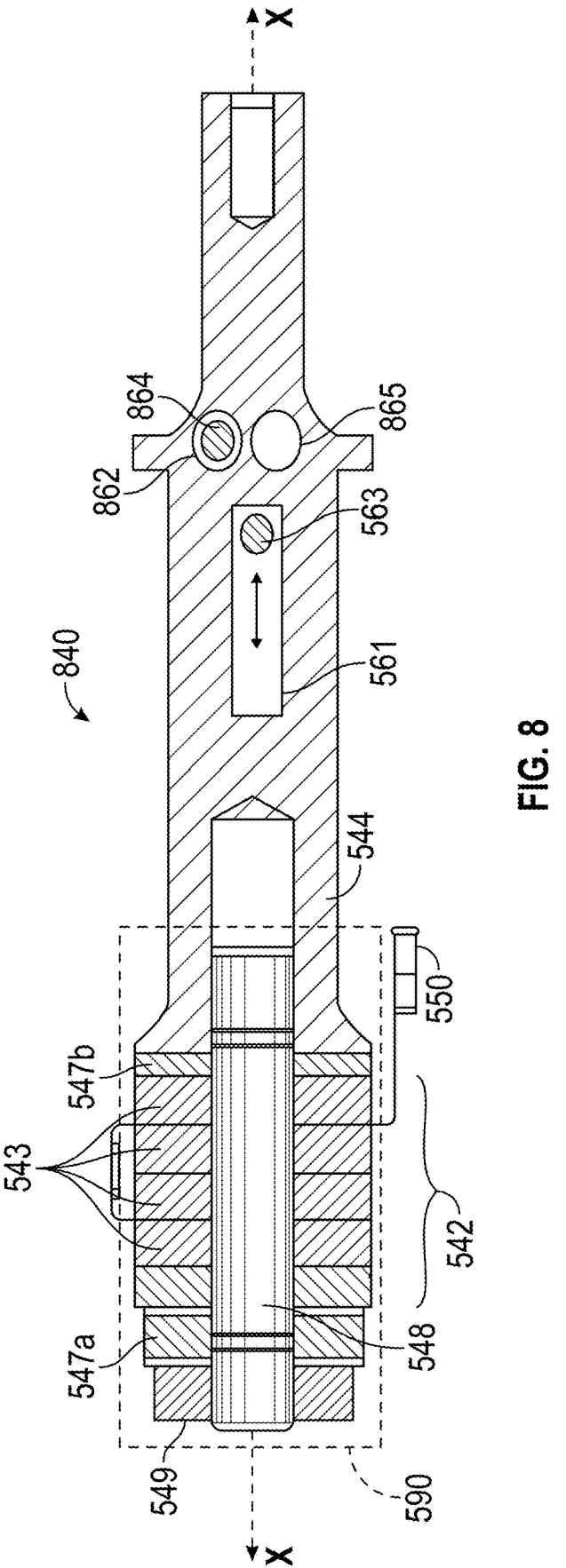
FIG. 8 is a longitudinal, cross-sectional view of another ultrasonic transducer provided in accordance with the present disclosure and configured for use with the surgical systems of FIGS. 1-4 or any other suitable surgical system.

Referring to FIG. 8, in ultrasonic transducer 840 a first transverse hole 862 including pivot pin 864 is positioned on a first side of the central axis X-X and a second transverse hole 865 is positioned on a second side of the central axis X-X opposite the first side. The first transverse hole 863 and the second transverse hole 865 may be symmetrically positioned with respect the central axis X-X. The first transverse hole 862 and/or the second transverse hole 865 may be laterally offset with respect to the central axis X-X. The first transverse hole 862 and/or the second transverse hole 865 may be laterally offset with respect to cam slot 561.

Other positionings and/or number of transverse holes and/or slots to facilitate balance are also contemplated.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An ultrasonic surgical system, comprising:
   an ultrasonic transducer configured to receive an electrical drive signal and, in response thereto, to produce ultrasonic mechanical motion that is output along an ultrasonic horn of the ultrasonic transducer, the ultrasonic horn defining a cam slot therein;
   a blade extending from the ultrasonic horn and configured to receive the ultrasonic mechanical motion from the ultrasonic horn for treating tissue in contact therewith;
   a jaw member movable relative to the blade between a spaced-apart position and an approximated position for clamping tissue therebetween; and
   a cam pin slidably disposed in the cam slot and operably coupled to the jaw member, wherein slidably advancing the cam pin in the cam slot pivots the jaw member relative to the blade between the spaced-apart position and the approximated position.

2. The ultrasonic surgical system of claim 1, further including a first transverse hole defined in the ultrasonic horn and a pivot pin disposed in the first transverse hole, wherein the pivot pin operably couples the jaw member to the blade.

3. The ultrasonic surgical system of claim 2, further including a second transverse hole formed in the ultrasonic horn, the second transverse hole configured to balance a transmission of the ultrasonic mechanical motion through the ultrasonic horn.

4. The ultrasonic surgical system of claim 3, wherein the second transverse hole is laterally offset with respect to the cam slot.

5. The ultrasonic surgical system of claim 3, wherein the ultrasonic transducer defines a central axis, and wherein the second transverse hole is laterally offset from the first transverse hole and the cam slot with respect to the central axis of the ultrasonic transducer.

6. The ultrasonic surgical system of claim 3, wherein the cam slot defines a proximal side and a distal side, and wherein the first transverse hole is positioned distal of the distal side of the cam slot and the second transverse hole is positioned proximal of the proximal side of the cam slot.

7. The ultrasonic surgical system of claim 3, wherein the ultrasonic transducer defines a central axis, and wherein the first transverse hole is positioned on a first side of the central axis and the second transverse hole is positioned on a second side of the central axis opposite the first side.

8. The ultrasonic surgical system of claim 1, further including an elongated assembly supporting the ultrasonic transducer, the elongated assembly defining at least one articulation joint, wherein the ultrasonic transducer is positioned distally of the at least one articulation joint.

9. The ultrasonic surgical system of claim 8, further including an ultrasonic generator configured to provide the electrical drive signal, the ultrasonic generator positioned proximally of the at least one articulation joint.

10. The ultrasonic surgical system of claim 8, further including a handle assembly supporting the elongated assembly, the elongated assembly extending distally from the handle assembly.

11. The ultrasonic surgical system of claim 1, wherein the ultrasonic transducer, the blade, the jaw member, and the cam pin form at least a portion of an end effector assembly configured to connect to a robotic arm of a robotic surgical system.

12. The ultrasonic surgical system of claim 1, wherein the ultrasonic transducer includes a piezoelectric stack maintained in pre-compression against the ultrasonic horn.

13. The ultrasonic surgical system of claim 12, wherein the piezoelectric stack maintained in pre-compression is directly between a proximal end mass and the ultrasonic horn.

14. The ultrasonic surgical system of claim 1, wherein the blade is directly attached to the ultrasonic horn.

15. The ultrasonic surgical system of claim 1, further including a waveguide disposed between and interconnecting the ultrasonic horn and the blade.

* * * * *